US00PP16661P3

(12) United States Plant Patent

Lim et al.

(10) Patent No.: US PP16,661 P3

(45) Date of Patent: Jun. 13, 2006

(54) SHRUB ROSE PLANT NAMED 'BAIKYE'

(50) Latin Name: *Rosa hybrida*
Varietal Denomination: BAIkye

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 84 days.

(21) Appl. No.: 10/972,676

(22) Filed: Oct. 26, 2004

(65) Prior Publication Data

US 2006/0090227 P1 Apr. 27, 2006

(51) Int. Cl.
*A01H 5/00* (2006.01)

(52) U.S. Cl. ..... Plt./108

(58) Field of Classification Search ..... Plt./108
See application file for complete search history.

*Primary Examiner*—Anne Marie Grunberg
*Assistant Examiner*—Annette H Para
(74) *Attorney, Agent, or Firm*—Buchanan Ingersoll PC

(57) ABSTRACT

A new and distinct variety of landscape shrub rose plant is provided which forms heavily in June in clusters and recurrently thereafter attractive fully double deep red blossoms that are blended with lighter shades creating an orange tone near the petal edge. The plant exhibits a compact upright rounded growth habit when grown in a cooler climate and a climbing growth habit when grown in a warmer climate. The attractive medium green glossy foliage contrasts nicely with the blossom coloration. The new foliage is tinted with red-purple coloration and the adult foliage is satiny medium green. High tolerance to Black Spot and Powdery Mildew is displayed. The plant can be grown to advantage to provide attractive ornamentation in parks and gardens.

2 Drawing Sheets

Botanical commercial classification: *Rosa hybrida*/Shrub Rose Plant.

Varietal denomination: cv. 'BAIkye'.

SUMMARY OF THE INVENTION

The new variety of *Rosa hybrida* landscape shrub rose plant was created at Yamhill, Oreg., U.S.A., during 1992 by artificial pollination wherein two parents were crossed which previously had been studied in the hope that they would contribute the desired characteristics. The female parent (i.e., the seed parent) was the 'INTerfire' variety (non-patented in the United States). The 'INTerfire' variety sometimes is known as the 'Darthuizer Orange Fire' variety and is marketed under the ORANGE FIRE trademark. The male parent (i.e., the pollen parent) was an unreleased plant from our breeding program designated '5-180A' (non-patented in the United States). The parentage of the new variety can be summarized as follows:

'INTERfire'×'5-180A'.

The seeds resulting from the above pollination were sown and plants were obtained which were physically and biologically different from each other. Selective study resulted in the identification during 1995 of a single plant of the new variety having the distinctive ornamental characteristics hereafter described.

It was found that the new variety of the present invention:

(a) exhibits a compact, upright rounded growth habit when grown in a cooler climate and a climbing growth habit in a warmer climate, (b) forms heavily in June in clusters and recurrently thereafter attractive double deep red blossoms that are blended with lighter shades creating an orange tone near the petal edge, (c) forms new foliage that is tinted with red-purple coloration and satiny medium green adult foliage, (d) displays high tolerance to Black Spot and Powdery Mildew; and (e) is particularly well suited for growing as attractive ornamentation in parks and gardens.

The young red buds open to orange-red blooms that fade to a lighter more orange shade with full maturity. The new variety serves well as an attractive shrub in cooler climates and a vigorous climber in warmer climates. The blossom coloration contracts nicely with the satiny medium green foliage.

The new variety well meets the needs of the horticultural industry. It can be grown to advantage where attractive ornamentation is desired, such as in parks and gardens.

The new variety can be readily distinguished from its parental varieties. More specifically, the 'INTerfire' variety is a Floribunda that forms bright orange-pink urn-shaped blossoms of approximately 15 to 20 petals having a diameter of approximately 8 cm that are borne in sprays.

The new variety also can be readily distinguished from other shrub rose varieties such as the 'AUSmum' (U.S. Plant Pat. No. 9,527) and 'BAIoon' (U.S. Plant patent application Ser. No. 11/014,953, filed Dec. 20, 2004) varieties. More specifically, the 'AUSmum' variety forms larger blossoms having more petals that are orange to orange-red in coloration. The 'BAIoon' variety forms smaller blossoms having considerably more petals that are yellow in coloration.

The new variety has been found to undergo asexual propagation by budding on an understock beginning in August 1993 and by the rooting of cuttings. 'Dr. Huey' rootstock was used during the budding. Such asexual propagation by these techniques at Yamhill, Oreg., and at Phoenix, Ariz. has shown that the characteristics of the new variety are stable and are strictly transmissible by such asexual propagation from one generation to another. Accordingly, the new variety reproduces true to type. The new variety grows well on its own roots.

Initially the new plant was designated 92N407, and was evaluated during 2002 and 2003 under the designation 02R510. The new variety subsequently has been named the 'BAlkye', and currently is being marketed while using the GARDEN JUBILEE and SIERRA SKYE trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn., U.S.A. during the 2003 season.

DETAILED DESCRIPTION

Figure 1:
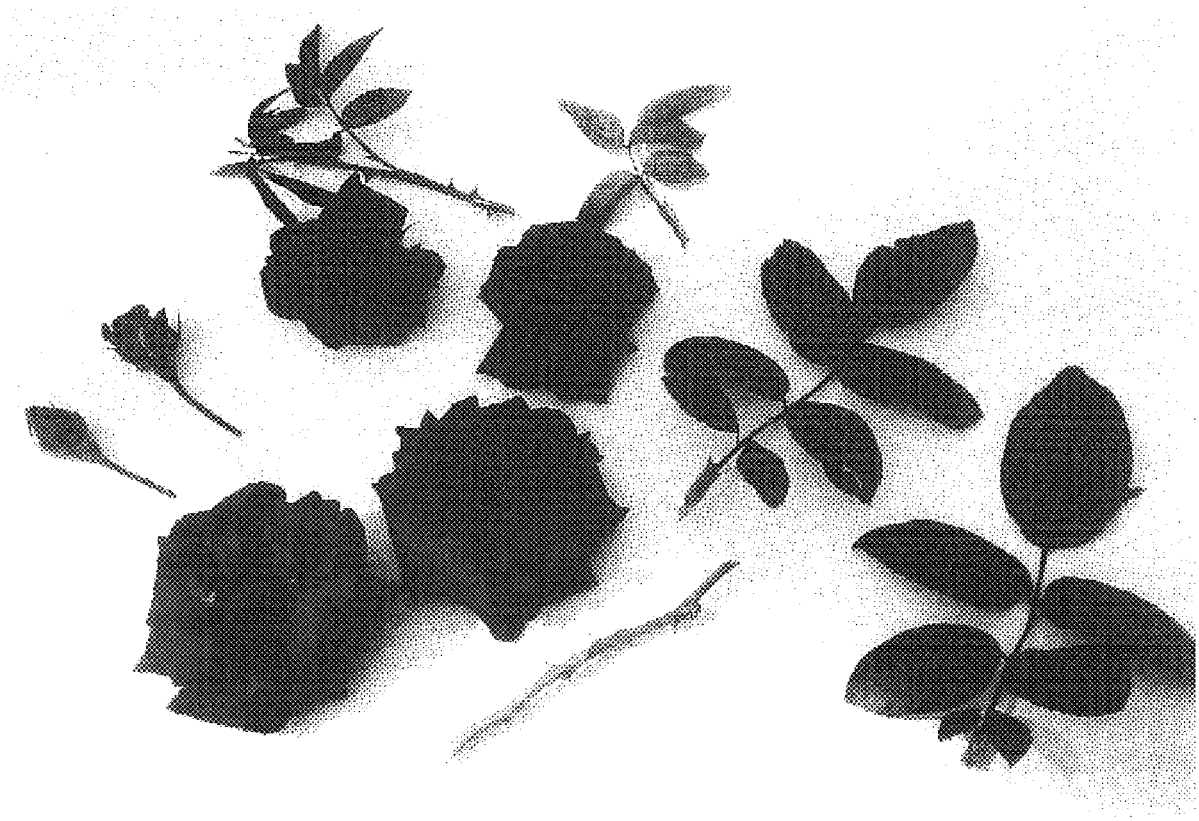
FIG. 1 illustrates typical plant parts of the new variety including buds, newly-opened blossoms, mature blossoms, a new shoot, five and seven-leaflet leaves, and a stem.
Figure 2:
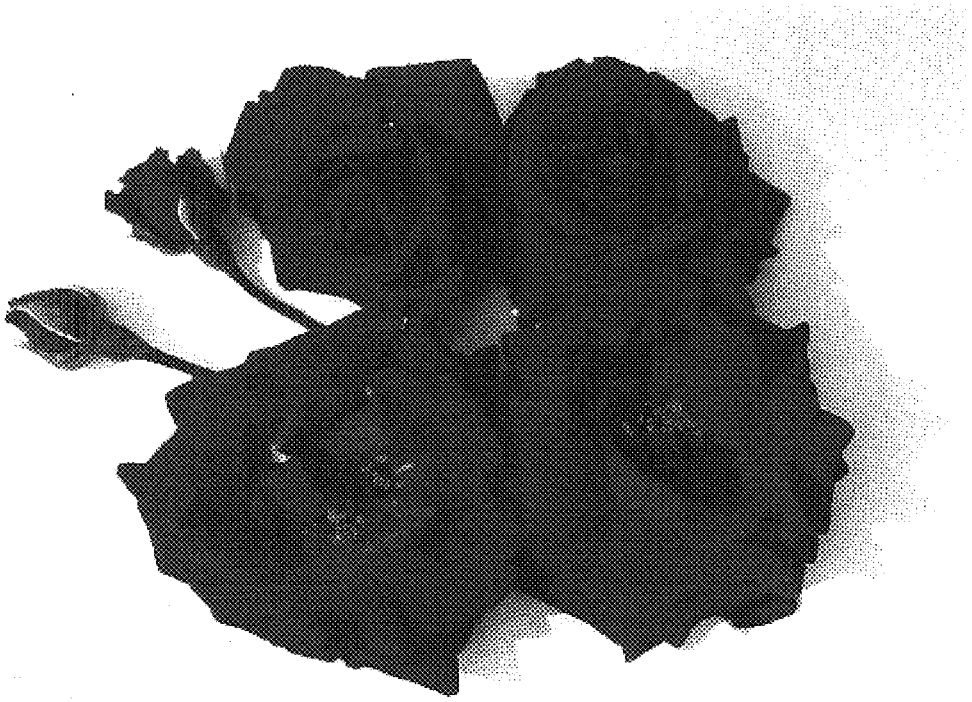
FIG. 2 illustrates a typical opening bud, a newly-opened flower, and blossoms in various stages of maturity.
Figure 3:
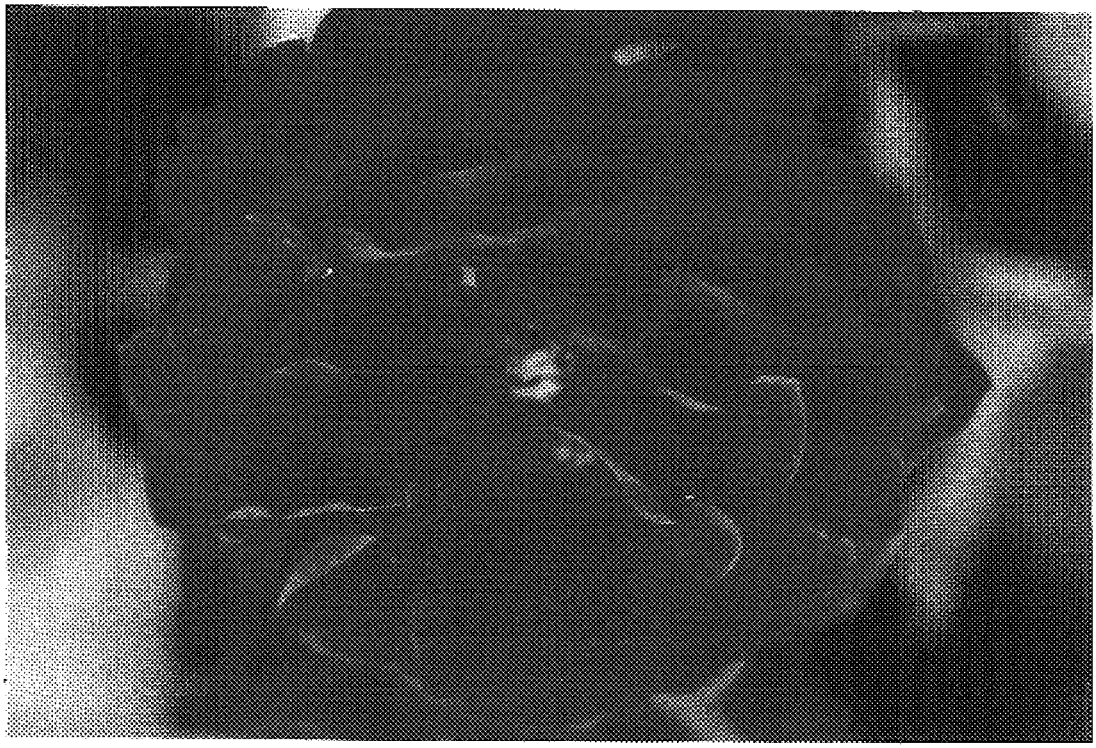
FIG. 3 illustrates a fully opened mature blossom that has begun to assume more orange coloration.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2003, at St. Paul, Minn., U.S.A., and at Yamhill, Oreg., U.S.A.

Botanical classification: *Rosa hybrida,* var. 'BAlkye'.
Class: Landscape Shrub.
Plant:
- *Height.*—Approximately 80 cm to 1.5 m on average at the end of the growing season.
- *Width.*—Approximately 90 cm on average at the end of the growing season.
- *Habit.*—A compact, dense, and upright rounded shrub in U.S.D.A. Hardiness Zone Nos. 4 and 5, and a climber in U.S.D.A. Hardiness Zone Nos. 6 to 9.

Branches:
- *Color.*—Young stems: Greyed-Purple Group 187B with highlights of Yellow-Green Group 146B. Adult wood: Greyed-Green Group 197A with streaks of Grey-Brown Group 199D.
- *Thorns.*—Size: commonly approximately 0.75 cm in length on average. Color: between Greyed-Purple Group 187B and 187C.

Leaves:
- *Stipules.*—Generally parallel with the auricle facing outward.
- *Petioles.*—Upper surface: Greyed-Purple Group 187B. Under surface: Yellow-Green Group 144C.
- *Leaflets.*—Number: 3, 5 (most often), and 7. Shape: ovate with a rounded base and an acuminate tip. Margin: serrulate. Texture: bears a satiny finish. General appearance: medium green with a satiny surface when mature. Color (young foliage): upper surface: between Greyed-Purple Group 187A and 187B. Under surface: Greyed-Purple Group 187A. Color (adult foliage): upper surface: Yellow-Green Group 147A. Under surface: between Yellow-Green Group 146A and 146B.

Inflorescence:
- *Number of flowers.*—Commonly approximately 4 blooms on average per cluster.
- *Peduncle.*—Greyed-Purple Group 187B with highlights of Yellow-Green Group 144A.
- *Sepals.*—Upper surface: Yellow-Green Group 148B with some pubescence. Under surface: Yellow-Green Group 146B with highlights of Yellow-Green Group 144B and Greyed-Purple Group 187B and 187C. Size: approximately 2.25 cm in length on average.
- *Buds.*—Shape: round to oval. Size: medium. Length: approximately 2.15 cm on average. Diameter: approximately 2.0 cm on average. Color: upper petal surface: Red Group 45A and 46A. Under petal surface: Red Group 53A.
- *Flower.*—Shape: fully double. Diameter: approximately 7.0 cm on average. Color (when opening begins): upper surface: Red Group 45A blending to Red Group 44A on the outer edge. Under surface: between Red Group 45A and 45B. Color (when blooming): upper surface: Red Group 43A blending to Red Group 43B and 43C at the base. Under surface: between Red Group 45B and 45C towards the basal petal spot. Color (at end of blooming): upper surface: Red Group 44B blended with Red Group 43B. Under surface: Red Group 45C with highlights of Red Group 45D. Color (basal petal spot): Yellow Group 2D. Fragrance: mild honey. Lasting quality: the blossoms commonly last approximately 3 to 6 days on average depending upon the temperature and sunlight exposure. Petal number: commonly approximately 28 to 32, and approximately 30 on average under normal growing conditions. Petal shape: wedge-shaped with a curled apex and recurved edges. Petal drop: commonly the petals detach cleanly at full blossom maturity. Anthers: Yellow-Orange Group 16A with a center of Red Group 46B. Filament number: commonly approximately 122 on average. Filament color: Red Group 45C. Pistils: approximately 60 on average. Stigmas: Yellow Group 2C in coloration. Styles: Yellow Group 3D with highlights of Red Group 44C. Receptacle: separate and free.

Development:
- *Vegetation.*—Compact shrub in cooler zones and a climber in warmer zones.
- *Blooming.*—Heavy in June and recurrently thereafter.
- *Resistance to diseases.*—Highly tolerance to Black Spot and Powdery Mildew.
- *Hardiness zone.*—U.S.D.A. Hardiness Zone Nos. 5 to 9.

We claim:

1. A new and distinct variety of landscape shrub rose plant characterized by the following combination of characteristics:

(a) exhibits a compact, upright rounded growth habit when grown in a cooler climate and a climbing growth habit when grown in a warmer climate, (b) forms heavily in June in clusters and recurrently thereafter attractive double deep red blossoms that are blended with lighter shades creating an orange tone near the petal edge, (c) forms new foliage that is tinted with red-purple coloration and satiny medium green adult foliage, (d) displays high tolerance to Black Spot and Powdery Mildew; and (e) is particularly well suited for growing as attractive ornamentation in parks and gardens;

substantially as herein shown and described.

* * * * *